(12) United States Patent
Eltorai et al.

(10) Patent No.: US 12,233,280 B2
(45) Date of Patent: Feb. 25, 2025

(54) ADHESIVE PHOTOTHERAPY METHOD, SYSTEM, AND DEVICES FOR ACNE

(71) Applicant: Azulite, Inc., Old Saybrook, CT (US)

(72) Inventors: Adam E. M. Eltorai, Old Saybrook, CT (US); Daniel Gertrudes, Providence, RI (US); Don Nguyen, Warwick, RI (US)

(73) Assignee: Azulite, Inc., Old Saybrook, CT (US)

( * ) Notice: Subject to any disclaimer, the term of this patent is extended or adjusted under 35 U.S.C. 154(b) by 31 days.

(21) Appl. No.: 16/045,861

(22) Filed: Jul. 26, 2018

(65) Prior Publication Data

US 2020/0030627 A1 Jan. 30, 2020

(51) Int. Cl.
*A61N 5/06* (2006.01)

(52) U.S. Cl.
CPC .......... *A61N 5/0616* (2013.01); *A61N 5/062* (2013.01); *A61N 2005/0645* (2013.01); *A61N 2005/0649* (2013.01); *A61N 2005/0651* (2013.01); *A61N 2005/0663* (2013.01)

(58) Field of Classification Search
CPC .... A61N 2005/0643; A61N 2005/0645; A61N 2005/0647; A61N 5/0616; A61N 5/062; A61N 5/0613; A61N 5/0619; A61N 5/0624; A61N 2005/063; A61N 2005/0631; A61N 2005/0635; A61N 2005/0642; A61N 2005/0649; A61N 2005/065; A61N 2005/0651; A61N 2005/0652; A61N 2005/0653; A61N 2005/067; A61N 2005/073; A61N 2005/0662; A61N 2005/0663; A61N 2005/067073; H01M 50/284; H01M 50/287; H01M 50/20–298; H01M 2220/00; H01M 2220/30; F21V 23/04; F21V 23/0414; F21V 23/0421
See application file for complete search history.

(56) References Cited

U.S. PATENT DOCUMENTS 5,549,660 A * 8/1996 Mendes ............... A61N 5/0616
606/3
9,415,237 B2 * 8/2016 Wagenaar Cacciola ....................
A61N 5/0616
(Continued)

FOREIGN PATENT DOCUMENTS

WO  WO-2009081910 A1 * 7/2009  ........... A61N 5/0616
WO  WO-2010087559 A1 * 8/2010  ........... A61N 5/0619

*Primary Examiner* — Kevin C Sirmons
*Assistant Examiner* — Leah J Swanson
(74) *Attorney, Agent, or Firm* — Armis IP Law, LLC

(57) ABSTRACT

A phototherapy device, system, and method for treating acne and/or acne scarring, includes a light emitting device configured and arranged to emit light from a bottom surface thereof; and an attachment portion having an aperture therethrough configured to permit light through. The attachment portion is configured to retain the device to a user's skin and bathe the skin with phototherapeutic light from the light emitter. Attachment of the device may be preceded with the application of synergistic fluid, ointment, gel, cream, lotion, foam, soap, or other solutions which may or may not consist of known topical acne treatment agents, augment device attachment to the skin, and/or have photodynamic properties. The light emitted may be any wavelength, combinations of wavelengths, intensity, pulse frequency, and exposure duration.

13 Claims, 10 Drawing Sheets

(56) References Cited

U.S. PATENT DOCUMENTS

| | | | |
|---|---|---|---|
| 2004/0136186 A1* | 7/2004 | Hsu | F21V 23/0414 |
| | | | 362/208 |
| 2009/0043294 A1* | 2/2009 | Island | A61B 18/203 |
| | | | 606/9 |
| 2012/0207532 A1* | 8/2012 | Ho | A61N 5/0616 |
| | | | 401/209 |
| 2012/0289885 A1* | 11/2012 | Cottrell | A61N 5/0616 |
| | | | 604/20 |
| 2016/0236007 A1* | 8/2016 | Khan | A61N 5/0624 |
| 2016/0361564 A1* | 12/2016 | Pai | F21V 23/023 |
| 2018/0015297 A1* | 1/2018 | Kahn | A61N 5/0619 |

\* cited by examiner

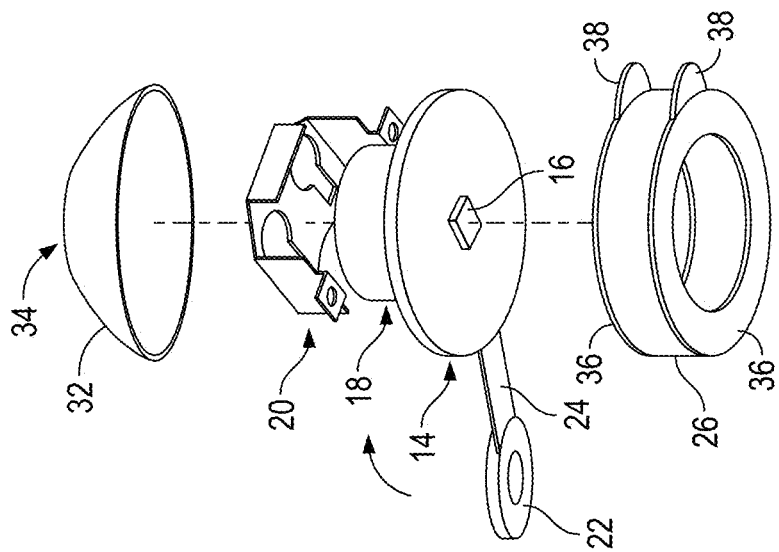
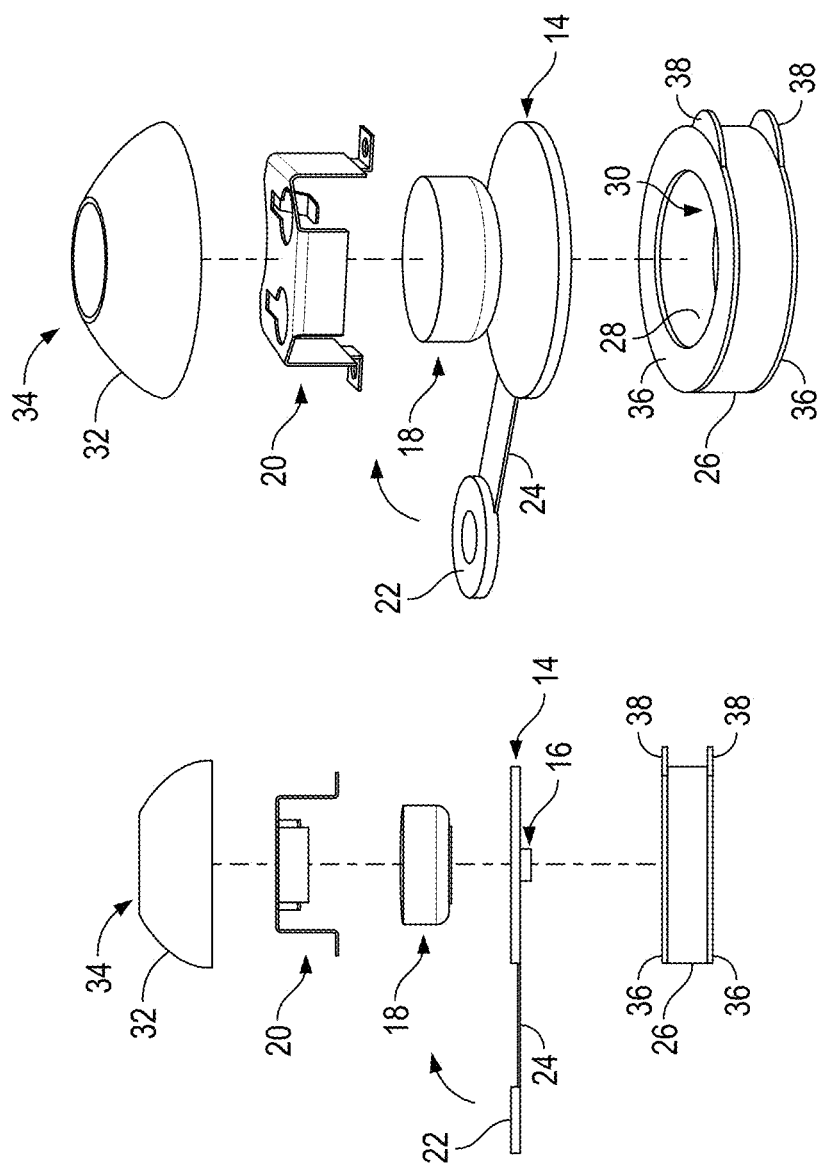
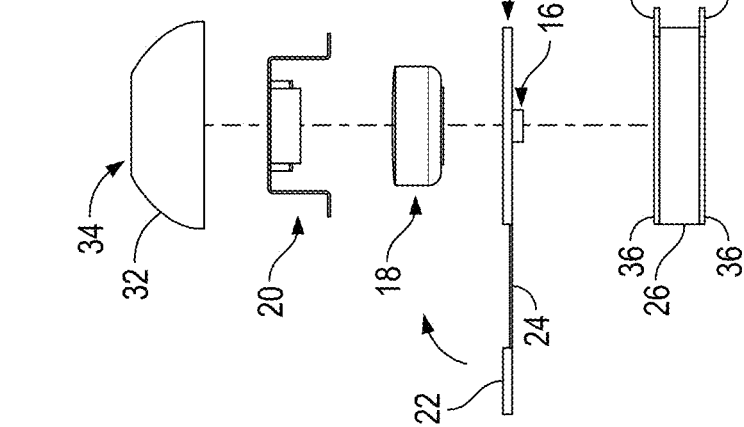
FIG. 6C
FIG. 6B
FIG. 6A

ADHESIVE PHOTOTHERAPY METHOD, SYSTEM, AND DEVICES FOR ACNE

FIELD OF THE INVENTION

The present patent document relates generally to methods for treating acne, and more particularly to a phototherapy device, system, and method of treating of acne and acne scars.

BACKGROUND OF THE INVENTION

Acne, also known as acne vulgaris is a common cutaneous disorder which can affect adolescents and young adults alike. Acne is a long-term skin disease that occurs when hair follicles are clogged with dead skin cells and oil from the skin. It is characterized by blackheads or whiteheads, pimples, oily skin, and possible scarring. It primarily affects areas of the skin with a relatively high number of oil glands, including the face, upper part of the chest, and back. The resulting appearance can lead to anxiety, reduced self-esteem and, in extreme cases, depression or thoughts of suicide. Patients that suffer from this condition can additionally experience significant scaring of the skin which can result in psychological side effects. Thus, there has been much research into prevention of acne vulgaris and reduction of the resulting scaring. In 2015, acne was estimated to affect 633 million people globally, making it the 8th most common disease worldwide. Acne commonly occurs in adolescence and affects an estimated 80-90% of teenagers in the Western world. Children and adults may also be affected before and after puberty. Although acne becomes less common in adulthood, it persists in nearly half of affected people into their twenties and thirties and a smaller group continue to have difficulties into their forties. Typical features of acne include increased secretion of oily sebum by the skin, microcomedones, comedones, papules, nodules (large papules), pustules, and often results in scarring. The appearance of acne varies with skin color. It may result in psychological and social problems.

Genetics is thought to be the primary cause of acne in 80% of cases. The role of diet and cigarette smoking is unclear, and neither cleanliness nor exposure to sunlight appear to play a part. During puberty, in both sexes, acne is often brought on by an increase in hormones such as testosterone. A frequent factor is excessive growth of the bacterium Propionibacterium acnes, which is normally present on the skin.

Many treatment options for acne are available, including lifestyle changes, medications, and medical procedures. Eating fewer simple carbohydrates such as sugar may help. Topical treatments applied directly to the affected skin, such as azelaic acid, benzoyl peroxide, salicylic acid, tretinoin, adapalene, tazarotene, isotretinoin, clindamycin, erythromycin, dapsone, topical combination products (benzoyl peroxide and clindamycin; benzoyl peroxide and erythromycin; clindamycin and tretinoin; benzoyl peroxide and adapalene), are commonly used. Antibiotics and retinoids are available in formulations that are applied to the skin and taken by mouth for the treatment of acne. However, resistance to antibiotics may develop as a result of antibiotic therapy. Acne is additionally treated with topical creams and cleansers, in addition to the aforementioned prescription antibiotics, anti-inflammatory medications, and vitamin A derivatives, which can have harmful side effects or adverse reactions. Several types of birth control pills help against acne in women. Isotretinoin pills are usually reserved for severe acne due to greater potential side effects. Early and aggressive treatment of acne is advocated by some in the medical community to decrease the overall long-term impact to individuals.

Acne scars are caused by inflammation within the dermal layer of skin and are estimated to affect 95% of people with acne vulgaris. The scar is created by abnormal healing following this dermal inflammation. Scarring is most likely to take place with severe acne but may occur with any form of acne vulgaris. Acne scars are classified based on whether the abnormal healing response following dermal inflammation leads to excess collagen deposition or loss at the site of the acne lesion. Atrophic acne scars have lost collagen from the healing response and are the most common type of acne scar (account for approximately 75% of all acne scars). They may be further classified as ice-pick scars, boxcar scars, and rolling scars. Ice-pick scars are narrow (less than 2 mm across), deep scars that extend into the dermis. Boxcar scars are round or ovoid indented scars with sharp borders and vary in size from 1.5-4 mm across. Rolling scars are wider than icepick and boxcar scars (4-5 mm across) and have a wave-like pattern of depth in the skin. The scars may also cause psychological and social problems.

Phototherapy using non-ultraviolet light has been shown to be effective at treating acne. While ultraviolet (UV) light has carcinogenic effects when exposed to the skin, non-UV light has been shown to be non-carcinogenic. Certain non-UV light wavelengths (such as visible light spectrum) possess antimicrobial effects, which are demonstrated to kill the bacteria causing acne. Some examples of light-based therapies include: broad-spectrum continuous-wave visible light sources (blue light, red light); intense pulsed light; laser sources including the potassium titanyl phosphate (KTP) laser, pulsed dye laser (PDL), and infrared lasers, photodynamic therapy; and photopneumatic technology. Clinician-administered light sources can be complex systems which require extensive training to use. At home light base therapies can be safe, effective, and can result in minimal complications when used according to the manufacturer's instructions. However, such at home light therapies can suffer from several deficiencies including the need for the user to hold the device in place for the entirety of the light therapy, thereby limiting the user to the use of one free hand—at best.

Current acne phototherapy devices require the patient to actively hold the phototherapy apparatus in place for the entirety of the light therapy session, thereby limiting the user to one free hand to perform any other activities. Other over the counter acne phototherapy devices can require a user sit in front of a stand mounted device which can preclude engagement in other activities. Such prior art devices affect the patient's ability to continue their normal activities of daily living, by tying up the user's hands or requiring the patient to sit still during treatment.

In another method of treatment, a full-face phototherapy mask may be used. Full face masks can enable hands-free phototherapy without the need for a user to sit at a stand. However, a mask has the disadvantage of being difficult to see out of during user and is only usable on the face. The user's impaired vision affects the user's ability to continue their normal activities of daily living.

Each of the issues above affects a patient's adherence to the clinical recommendation. Poor adherence reduces the efficacy of the therapeutic device. To improve adherence and, in turn, efficacy, the above issues need to be overcome. An improved device needs to require minimal behavioral change for the user and needs to allow the user to continue in their regular activities; an improved device should not occupy their hands, require them to be seated for prolonged periods of time in one place, nor obstruct their vision. Such requirements are particularly important given the demographic most commonly affected by acne—young, active teenagers and adults—who are generally on the move.

SUMMARY OF THE INVENTION

The phototherapy devices, systems, and methods disclosed herein solve the problems of the prior art by providing a phototherapy device that does not require a user to hold the device, sit in front of the device, or obstruct the user's vision. The devices do not require active engagement from the user during use, and therefore the user can avoid behavioral changes that have traditionally reduced adherence and effectiveness. Additionally, the device may be used on any area of the body.

In a first embodiment, the phototherapy device can include a light emitter configured and arranged to emit light from a bottom surface thereof; and a suction cup having an aperture therethrough. The light emitter can be configured and arranged to emit light through the aperture of the suction cup. The suction cup can be an integral, or separate, feature of the housing of the device. The suction cup can be flexible to permit the device to attach to a variety of contoured skin surfaces. Device attachment may be enhanced through the application of a fluid, ointment, gel, cream, lotion, foam, soap, or other solution. The fluid, ointment, gel, cream, lotion, foam, soap, or other solution may include known topical acne treatment, such as azelaic acid, benzoyl peroxide, salicylic acid, tretinoin, adapalene, tazarotene, isotretinoin, clindamycin, erythromycin, dapsone, topical combination products (benzoyl peroxide and clindamycin; benzoyl peroxide and erythromycin; clindamycin and tretinoin; benzoyl peroxide and adapalene). The light emitted may be varied for any wavelength or wavelength combinations of any intensities, pulse frequency, and exposure duration for phototherapeutic effects.

In an alternative embodiment, the phototherapy device can include a light emitter that is configured and arranged to emit light from a bottom surface thereof; and a pad having a first side with adhesive thereon, a second side opposite the first side, and an aperture therethrough. The pad can be connected to the bottom surface of the light emitter. The light emitter can be configured and arranged to emit light through the aperture of the pad. An optional case may hold the light emitter and a number of disposable pads as a kit.

BRIEF DESCRIPTION OF THE DRAWINGS

These and other features, aspects, and advantages of the present invention will become better understood with reference to the following description, appended claims, and accompanying drawings where:

FIG. 6A is an exploded elevation view of an exemplary embodiment of a phototherapy device FIG. 6B is an exploded top view of an exemplary embodiment of a phototherapy device FIG. 6C is an exploded bottom view of an exemplary embodiment of a phototherapy device;

DESCRIPTION OF THE PREFERRED EMBODIMENT

As will be described in greater detail below, the phototherapy devices, system, and methods are described herein. The devices can generally include a light emitter and an attachment device with an aperture that attaches to the light emitter. The attachment device can permit the device and the associated housing to removably attach to a user's skin at a variety of locations without concern for where the device is going to be used. Further, the attachment device advantageously allows for application of light-based phototherapy without the need for the user to continuously hold the device in place. Further still, the small foot print of the device advantageously will not obstruct the user's ability to see or perform other daily activities.

Figure 1A:
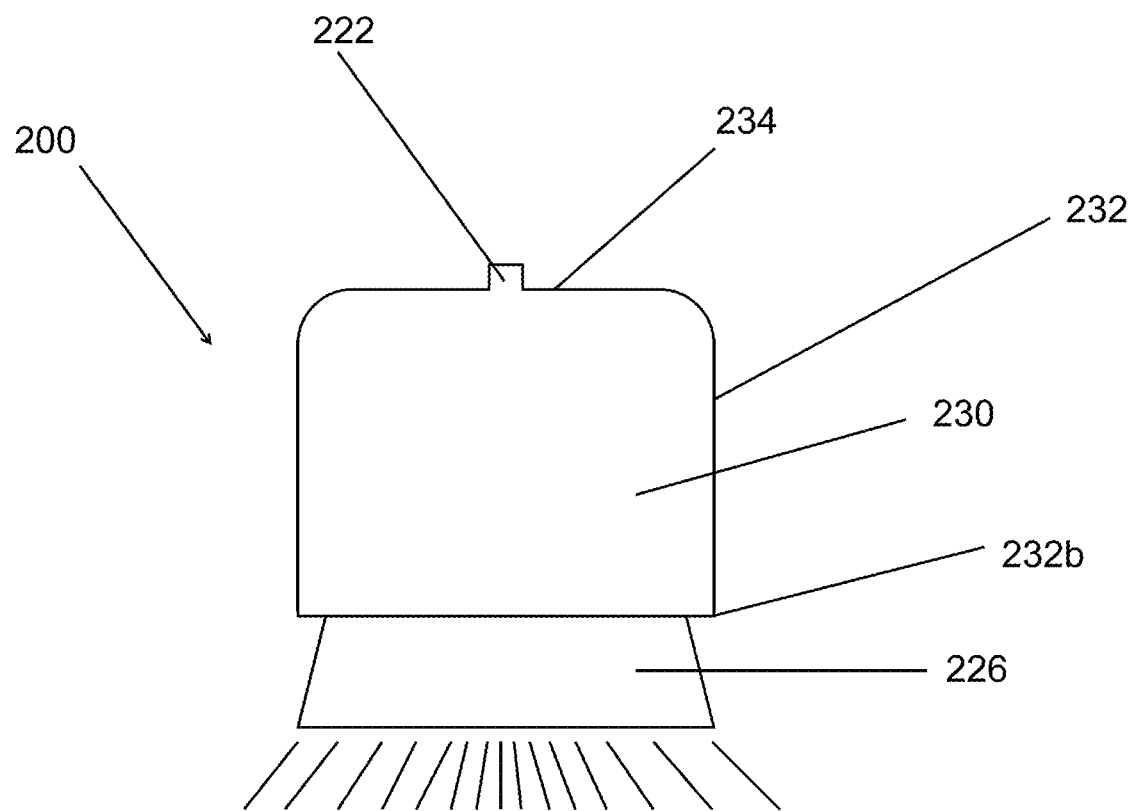
FIG. 1A is a side schematic view of a first exemplary embodiment of a phototherapy device.
Figure 1B:
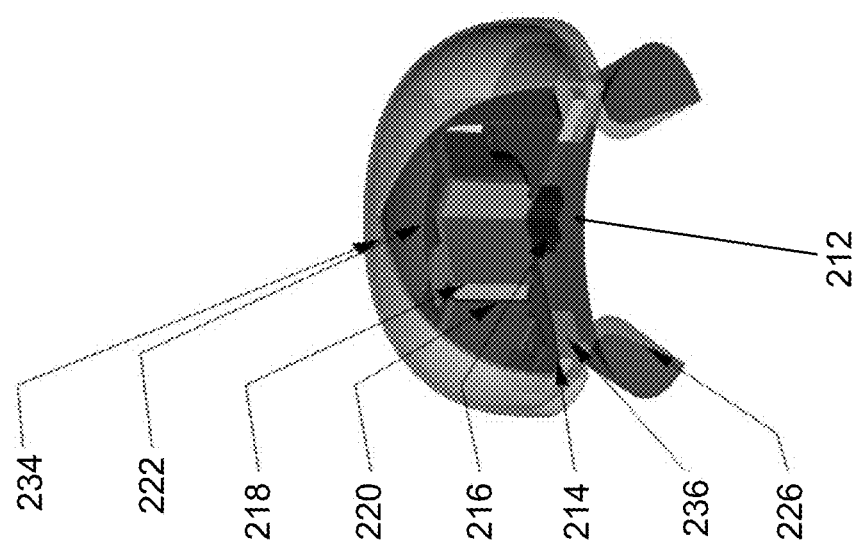
FIG. 1B is a partial cutaway perspective view of the device of FIG. 1A.

In a first embodiment, referring now to FIGS. 1A and 1B, a phototherapy device is shown generally at 200. The device can generally include a housing 230 and a light emitter 212. The housing 230 can be formed from materials including silicone, vinyl, rubber, and other materials including those having natural antimicrobial properties, or impregnated with antimicrobial materials. As shown, the housing 230 can generally include an upper most surface 234, a body portion 232, and a suction portion 226. The upper most surface 234 can have a protruding button 222 or can be flexible so that a user can interface with a button disposed therein. The button 222 can be used to operate the light emitter 212 as will be discussed further below. The housing 230 can be in the form of a dome like shell which can generally house the light emitter 212, a battery 218, and a programmable circuit board 214. In some embodiments, a stiffener 236 can support the programmable circuit board 214 within the housing 230. Depending downward from the lower end of the body 232*b*, a suction portion, or cup, 226 can extend. The suction cup 226 can include an aperture therethrough to permit light from the light emitter 212 to shine therethrough. The suction portion 226 can be compressible so that upon compression of the suction cup 226, air is evacuated, and a vacuum is created to retain the device 200 to the skin. In use, at the same time as the vacuum seal is created, the button 222 can be actuated in a single press to secure the device 200 to the skin and to activate the light emitter 212. Alternatively, the button 222 can be actuated separately from attaching the device 200 to the skin. In some use cases, it may be beneficial to apply a fluid, ointment, gel, cream, lotion, foam, soap, or other solution, to the skin before attachment of the device 200. In such a case, the suction cup 226 may have improved suction, and adhesion, to the skin. The fluid, ointment, gel, cream, lotion, foam, soap, or other solution can be azelaic acid, benzoyl peroxide, salicylic acid, tretinoin, adapalene, tazarotene, isotretinoin, clindamycin, erythromycin, dapsone, topical combination products (benzoyl peroxide and clindamycin; benzoyl peroxide and erythromycin; clindamycin and tretinoin; benzoyl peroxide and adapalene), each of which are medications used to treat mild to moderate acne. In some embodiments, medications used to treat mild to moderate acne can be enhanced by the phototherapy light device. Alternatively, the fluid, ointment, gel, cream, lotion, foam, soap, or other solution can be any of a composition and consistency which can have synergistic effects with the light. The fluid, ointment, gel, cream, lotion, foam, soap, or other solution can be provided in a tube, jar, or any other type of container. In some exemplary embodiments, the device 200 can be packaged with one or more containers of the fluid, ointment, gel, cream, lotion, foam, soap, or other solution. For example, a tube of synergistic fluid, ointment, gel, cream, lotion, foam, soap, or other solution can be provided in a single package with at least one device 200. In some examples, the package can include a plurality of tubes of synergistic fluid, ointment, gel, cream, lotion, foam, soap, or other solution, either the same kinds or different types, and a plurality of devices 200.

Figure 3:
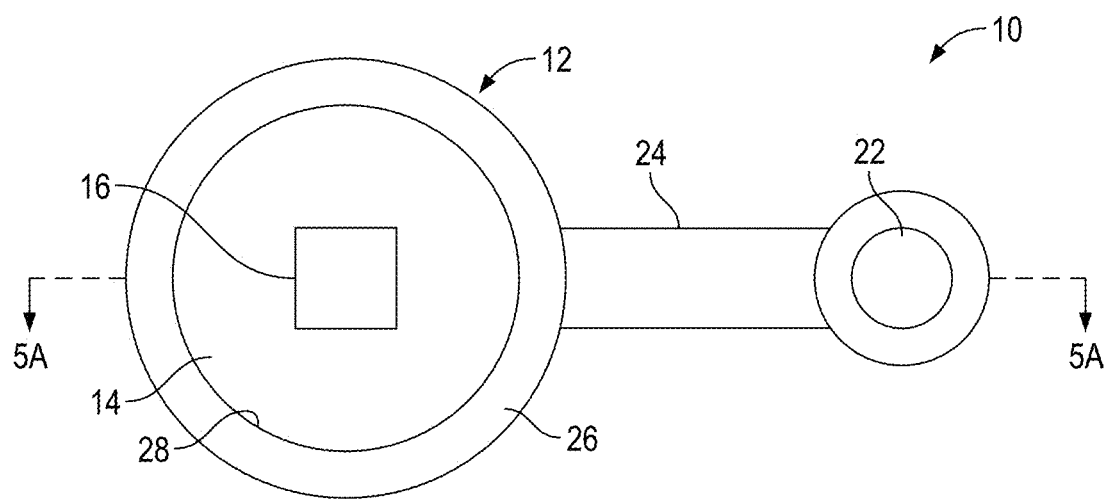
FIG. 3 is a bottom view of an alternative exemplary embodiment of a phototherapy device with a cover removed and a switch in an unfolded position.
Figure 4:
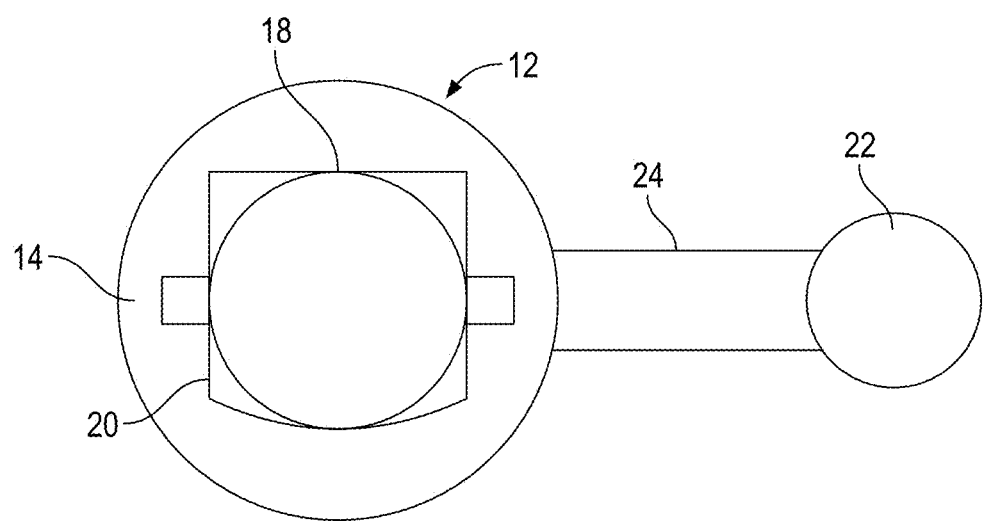
FIG. 4 is a top view of an exemplary embodiment of a phototherapy device with the cover removed and a switch in an unfolded position.

As noted above, the device 200 can generally include a light emitter 212 having a circuit board 214 with a light emitting diode ("LED") 216 on a bottom surface thereof. In a first embodiment, the LED 216 is a blue-light LED. Alternatively, the LED 216 can be a red-light LED, or a combination thereof. Further still, the LED 216 can be any type of light source which produces a therapeutic benefit. A battery 218 can be retained in a battery cage 220 on a top surface of the circuit board 214. The switch 222, such as a momentary switch, can be connected to the circuit board 214 with ribbon cable (not shown). A circuit can be formed with the LED 216, switch 222 and battery 218. The circuit can be programmed to operate the LED 216 for a predetermined time when the switch 222 is depressed. The circuit can be substantially the same as the circuit shown in FIGS. 3 and 4.

Figure 2:
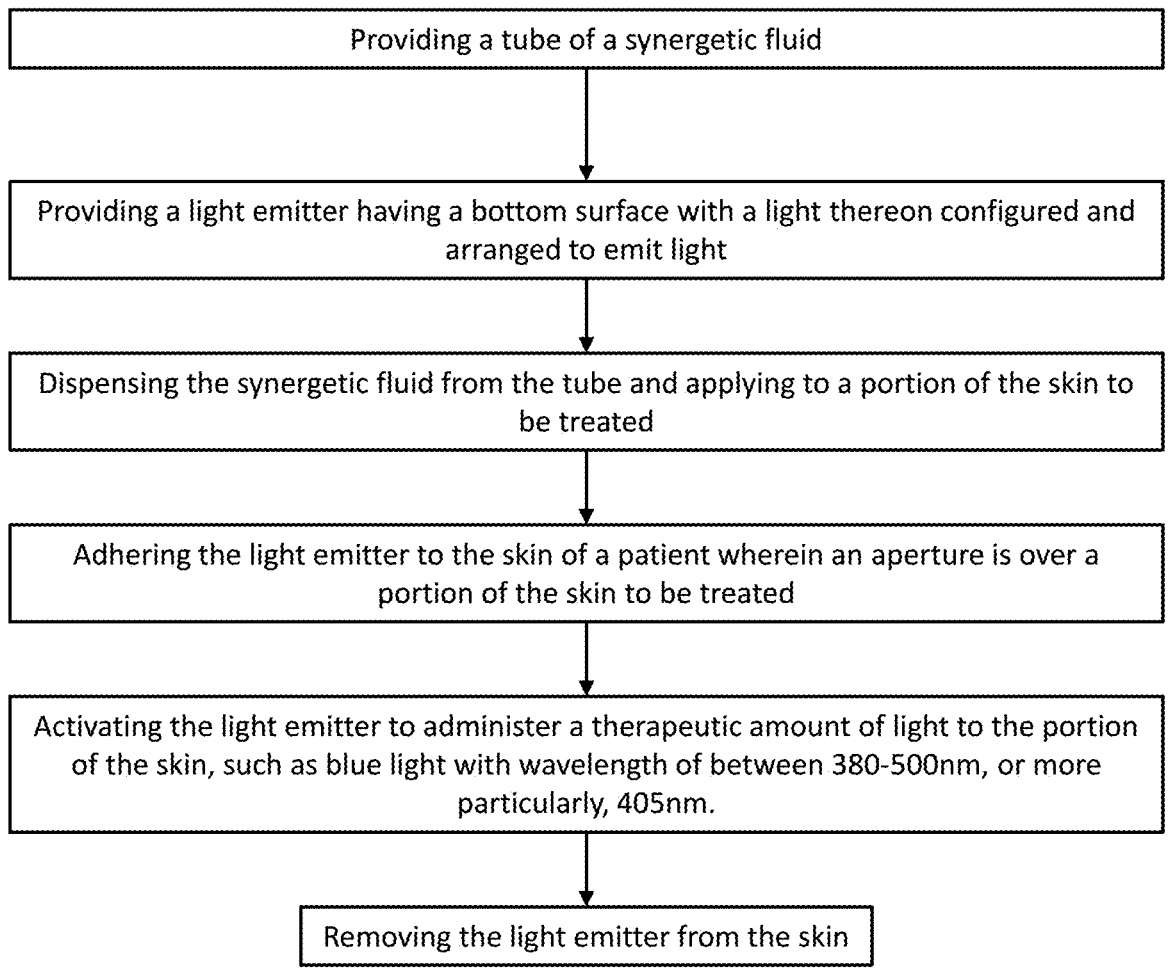
FIG. 2 is a flowchart of an exemplary method of using a phototherapy device of FIGS. 1A and 1B to treat a skin disorder

In a first exemplary method of use, as shown in FIG. 2, the user is provided with a pre-application, synergistic fluid, ointment, gel, cream, lotion, foam, soap, or other solution and a light emitting device in first and second method steps. The user can dispense the synergetic fluid, ointment, gel, cream, lotion, foam, soap, or other solution from a tube in a third step and optionally apply a layer of the gel to the area of the skin to be treated by the device. In one example, the area can be over an area of acne on the face, back, chest, or any other location on the human body. Alternatively, the application of the gel can be omitted. After the application of the gel, in a fourth step, the device can be adhered or pressed onto the skin, in the area of the gel. Pressing of the device can create a vacuum seal by the suction cup on the skin, in the fourth step, and simultaneously, can actuate the button to activate the light source to bathe the skin in light, in the fifth step. Alternatively, the creation of the vacuum and the activation of the button can be performed separately. After a predetermined amount of time, the light source can be deactivated, either automatically, or by pressing the switch again. The user can then lift a lip of the suction cup to release the vacuum seal and thereby release the device from the skin, in the sixth step. The exemplary method can be performed at various stages of the acne progression. For example, the method can be performed upon the emergence of a lesion to reduce the severity of the acne by killing pathogenic bacteria; during an active breakout of acne to expedite recovery, reduce the inflammation, reduce erythema and bacteria, and improve the overall outcome; or after the acne has cleared up to reduce scar formation and severity to improve the healing. Moreover, a user can perform the method during one, two or all the stages.

Referring now to FIGS. 3-7C, an embodiment of the phototherapy device is shown generally at 10. The device 10 generally includes a light emitter 12 having a circuit board 14 with a light emitting diode ("LED") 16 on a bottom surface thereof. A battery 18 is retained in a battery cage 20 on a top surface of the circuit board 14. A switch 22, such as a momentary switch is connected to the circuit board 14 with ribbon cable 24. A circuit is formed with the LED 16, switch 22 and battery 18 and is programmed to operate the LED 16 for a predetermined time when the switch 22 is depressed. A pad 26 is removably secured to the bottom surface of the circuit board 14. The pad 26 includes an inner surface 28 defining an aperture 30 for the LED 16.

Figure 5A:
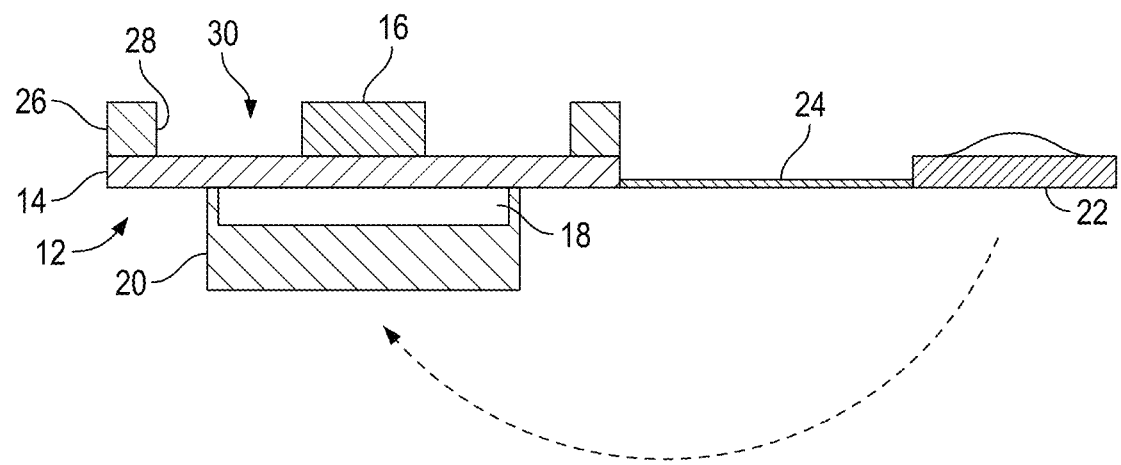
FIG. 5A is a cross-section view through line 5A-5A of FIG. 3, illustrating an exemplary embodiment of a phototherapy device with a switch in an unfolded position with the cover removed.
Figure 5B:
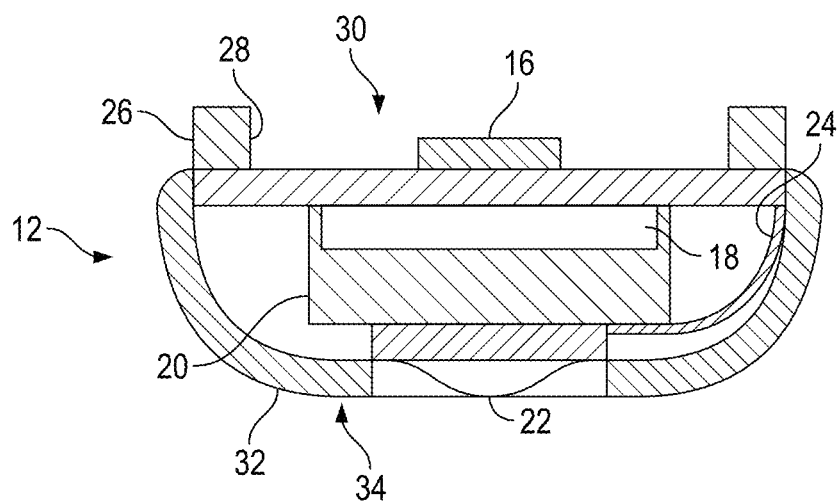
FIG. 5B is a side cross-section view illustrating an exemplary embodiment of a phototherapy device with a switch repositioned over a battery cage thereof and cover enclosing the device.
Figure 7A:
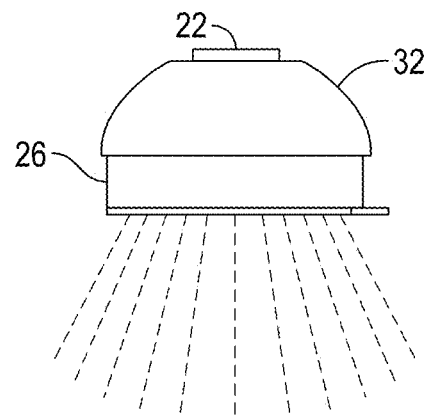
FIG. 7A is a side elevation view of an exemplary embodiment of a phototherapy device.
Figure 7B:
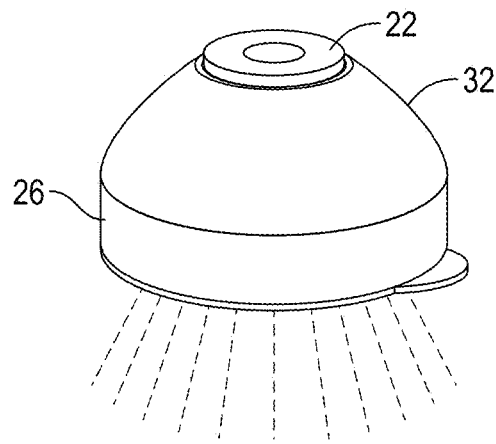
FIG. 7B is a top perspective view of an exemplary embodiment of a phototherapy device.
Figure 7C:
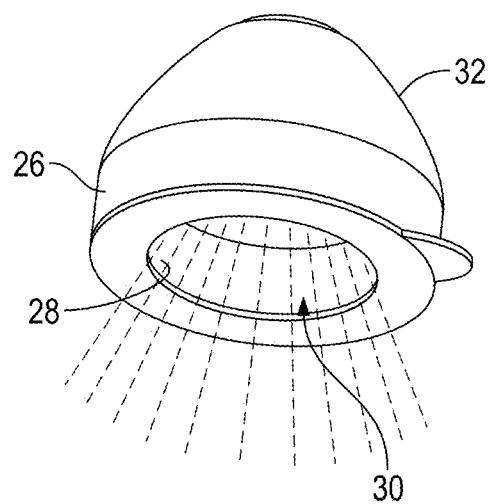
FIG. 7C is a bottom perspective view of an exemplary embodiment of a phototherapy device.

Referring to FIGS. 5A and 5B, the switch 22 is folded over the battery cage 20. Best seen in FIGS. 7A-7C, a cover 32 encloses the top surface of the circuit board 14, batter 18 and battery cage 22, leaving only the switch 22 exposed through an aperture 34 in the cover 32. The cover 32 may attach to the circuit board 14 via a snap-fit, twist-fit, threads and/or fasteners.

In one embodiment, the pad 26 may be ring-shaped; however, the pad 26 may have a different shape. Similarly, the aperture 30 in the pad 26 may be circular or have another profile. The profile of the aperture 30 need not be the same as the profile of the outer shape of the pad 30. For instance, the pad 26 may have a circular profile while the aperture 30 has a square profile. The pad 26 may be formed from a foam material having a thickness sufficient to elevate the circuit board 14 and LED 16 away from a person's skin. The pad 26 may include adhesive with a peelable, protective layer 36 on a top side and/or a bottom side of the pad (best seen in FIGS. 6A-6C). The protective layer may include a tab 38 to assist with removal of the protective layer 36 from the adhesive of the pad 26. The adhesive is preferably a weak adhesive, allowing the pad 26 to be removed from the device 10 and/or skin of the person without tearing of the pad 26, damage to the device 10, or discomfort to the person. The top surface of the pad 26 may be adhered to the device 10 and the bottom surface of the pad 26 adhered to the skin of the person.

Figure 8A:
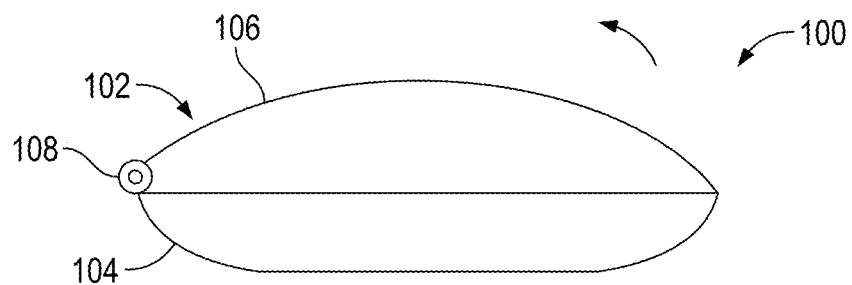
FIG. 8A is a side elevation view of an exemplary embodiment of a kit for a phototherapy device with a lid in a closed position.
Figure 8B:
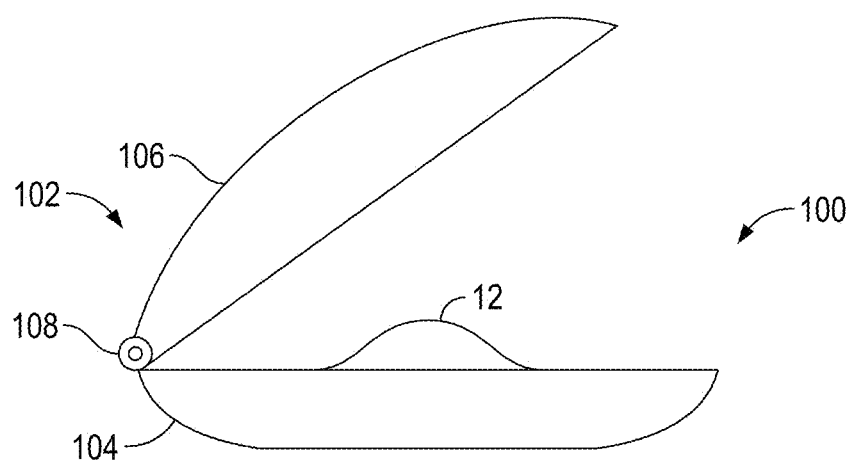
FIG. 8B is a side elevation view of an exemplary embodiment of a kit for a phototherapy device with a lid in an open position.
Figure 9:
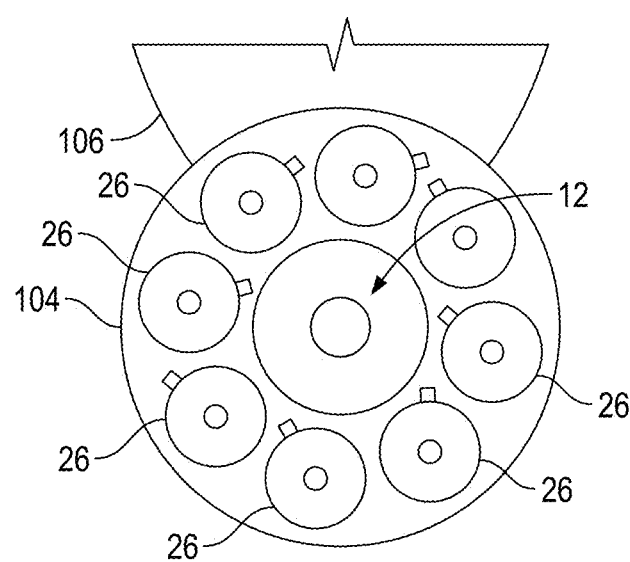
FIG. 9 is a partial top view of an exemplary embodiment of a kit for a phototherapy device with a lid in an open position.

Referring to FIGS. 8A, 8B and 9, an exemplary embodiment of a kit for a phototherapy device is shown generally at 100. The kit 100 may include a case 102 configured to hold a phototherapy device 10 having a light emitter 12 and a number of disposable pads 26.

In some embodiments, the case 102 may generally be in a clamshell configuration with a bottom portion 104 and a top portion 106 hinged to the bottom portion 104. The top portion 106 may pivotally open and close about the hinge 108. In one embodiment, the case 100 is circular, with a first location located in a center of the bottom portion 106 the case 100 to hold a light emitter 12 and a number of second locations located about the periphery of the bottom portion 106 of the case 100, configured to hold a number of disposable pads 26. Other case configurations may be used. The number of disposable pads 26 may be selected based on the number of treatments prescribed, such as 7-10, for example.

Depressing the switch 22 activates the LED 16 for a predetermine treatment period. For instance, a treatment period may be thirty minutes. After the treatment period lapses, the LED 16 is switched off. In addition, the light emitter 12 may deactivate after a specified total number of prescribed uses, such as 7-10 treatments. Optionally, the circuit board 14 may be further programmed to pulse, change the wavelength, or intensity of the emitted light from the LED 16 according to the prescribed treatment regimen.

The LED 16 may be configured to emit a non-UV light, such as blue light in wavelengths from 380 nm to 500 nm. In particular, blue light in wavelengths of about 405 nm may be used.

Figure 10A:
FIG. 10A is an illustration of a person applying an exemplary embodiment of a phototherapy device to their skin.
Figure 10B:
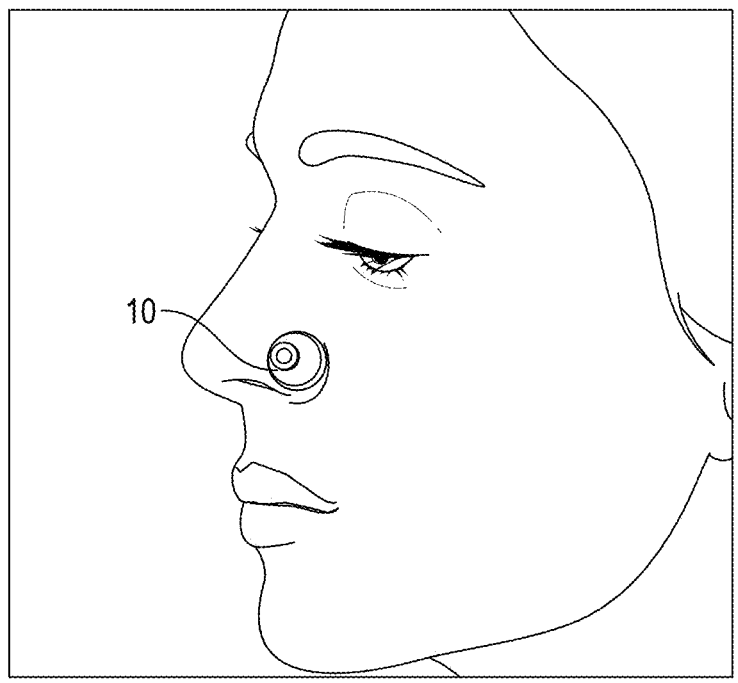
FIG. 10B is an illustration of a person with an exemplary embodiment of a phototherapy device applied to the skin.
Figure 11:
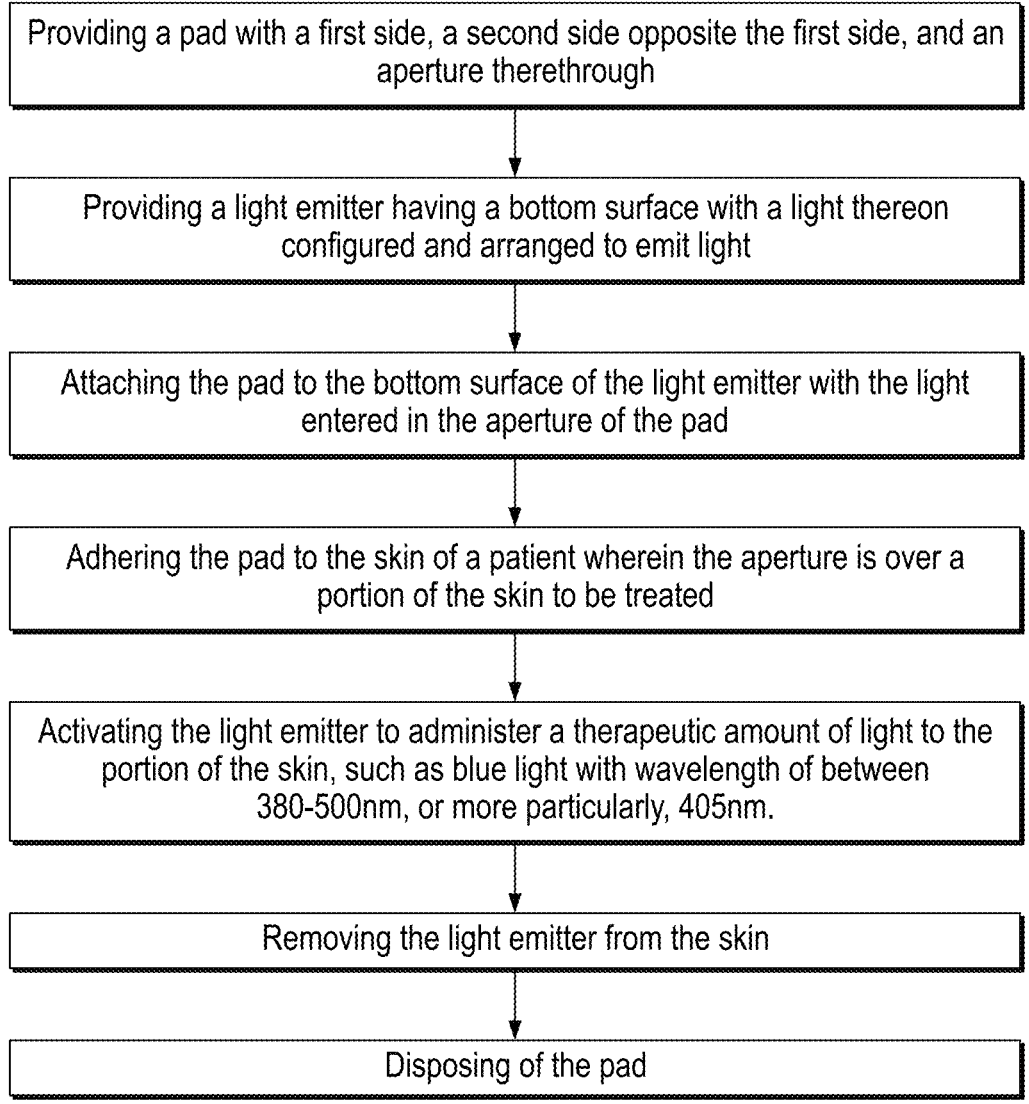
FIG. 11 is a flowchart of an exemplary method of using a phototherapy device to treat a skin disorder.

Referring to FIGS. 10A, 10B and 11, a method of using the phototherapy device of FIGS. 3-9, to treat a skin disorder such as acne, is shown generally.

In a first and second steps, the user is provided a pad and light emitter as described above, which may be in a case of the kit described above. In a third step, the user opens the case and selects a pad. The user then peels away the protective layer from one side of the adhesive of the pad and attaches the pad to the light emitter. In particular, the user removes the might emitter from the case and press the exposed first layer of adhesive of the pad onto the bottom surface of the device, being careful to center the pad on the device.

In a fourth step, the user peels away a protective layer from the other, exposed side of the pad, exposing the second layer of adhesive, and the device is then applied to the affected area of the skin with gentle pressure by pressing the exposed adhesive of the pad against skin. For example, in FIG. 10A, a person is illustrated placing the phototherapy device on a portion of the skin near the user's nose.

In a sixth step, the user then activates the device by pressing the switch. After the predetermined time period lapses in a seventh step, the device shuts off and alerts the user. For example, in FIG. 10B, a person is illustrated wearing the phototherapy device during treatment.

In a seventh and eighth steps, the user then removes the device from the skin and peels the pad from the device and disposes the pad. The device is returned to the case until the next treatment. The foregoing method can be performed at various stages of the acne progression. For example, the method can be performed upon the emergence of a lesion to reduce the severity of the acne by killing pathogenic bacteria; during an active breakout of acne to expedite recovery, reduce the inflammation, reduce erythema and bacteria, and improve the overall outcome; or after the acne has cleared up to reduce scar formation and severity to improve the healing. Moreover, a user can perform the method during one, two or all the stages.

Therefore, it can be seen that the present invention provides a unique solution to the problem of treating a skin disorder, such as acne, with phototherapy that does not require that the person hold the device or sit still during treatment. Furthermore, the user may remain active and use both hands for other tasks.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A phototherapy device for reducing acne and acne scars on a skin surface, comprising:
a housing including a body portion with a bottom surface and a top surface; the body portion encasing:
a switch, the switch aligned centrally in the top surface of the housing,
a battery having a cylindrical shape including a circular top side, a circular bottom side, and a curved side with a height less than a diameter of the circular sides,
a computer,
a light emitter configured and aligned centrally in the housing to emit light through an aperture on the bottom surface, and
a conductor for providing electrical communication between the switch and the computer, the battery and light emitter aligned with a targeted area of the skin surface;
an attachment portion defined by an adhesive pad configured between a circumference of the bottom surface and the skin surface, the adhesive pad configured to permit light passage through the bottom surface of the housing to the underlying skin, and to retain the housing to the skin surface for bathing the targeted area of the skin with light from the light emitter, the light configured to have therapeutic effects,
the adhesive pad adapted for application onto the targeted area with a topical treatment including therapeutic agents, the topical treatment aligned with the light for synergistic effects; and
a circuit board including:
the computer,
a connection to the switch, and
a battery cage extending over the circular top side of the battery for holding the battery, the connection to the switch defined by the conductor and extending from the circuit board and flexibly to the switch aligned with the top surface of the housing and operable by manual compression, the switch disposed on the battery cage for closing an electrical circuit between the light emitter and the circuit board, the light emitter disposed on an opposed side of the circuit board from the battery and directed towards the aperture in the bottom surface of the housing;
the battery cage having a top surface extending across a diameter of the top circular side of the battery and extending parallel to the circuit board and having at least one leg extending perpendicularly from the circuit board to the top surface and flanking the curved side of the battery, the circular bottom side of the battery disposed on the circuit board, and the circular top side of the battery facing the top surface of the battery cage, the battery cage securing the battery in contact with the circuit board, the top surface of the battery cage disposed between the switch and the battery, and the at least one leg defining a gap at least as wide as the height of the curved side for accommodating the battery between the top surface of the battery cage and the circuit board while the top and bottom circular sides of the battery remain parallel to the circuit board and parallel to the top surface of the battery cage;

the conductor flexibly extending from the circuit board around the top surface of the battery cage and connecting with the switch on top of the battery cage for closing the circuit at the switch in response to activation;

the switch accessible for closing the circuit through the top surface of the housing for electrical communication between the battery and the light emitter aligned with the topical treatment for direct irradiation of the targeted area of the skin through the adhesive pad.

2. The device of claim 1, wherein the emitted light is configured to exhibit at least one of optimized wavelengths of light, combination of wavelengths, intensity, pulse frequency, and exposure duration.

3. The device of claim 1, wherein the adhesive pad has a first side with adhesive thereon, a second side opposite the first side; the adhesive pad connected to the bottom surface of the body portion, wherein the adhesive pad is made from a compressible material, contains an aperture through which the light can pass, and comprising adhesive on the second side for attachment to the skin.

4. The device of claim 1, wherein the housing is configured for access to the switch.

5. The device of claim 1, wherein the body portion of the housing is secured to the circuit board by one of a snap-fit, twist-fit, and a thread.

6. The device of claim 1, wherein the light emitter is an LED.

7. The device of claim 6, wherein the computer is configured to perform at least one of turning light on/off, timing light duration, turning the light off after a certain duration, directing the light to pulse.

8. The device of claim 1, wherein the light emitter includes at least one LED.

9. The device of claim 1, wherein the attachment portion can be applied and removed from the bottom surface of the housing and the skin.

10. The device of claim 1, wherein the conductor connecting the switch and the computer further comprises a flexible, folded ribbon cable.

11. The device of claim 1, wherein the battery cage centrally aligns the battery for connection to the conductor.

12. The device of claim 1 wherein the switch closes an electrical connection between the battery and the conductor.

13. The device of claim 1, wherein the switch is disposed on the battery cage between the top surface and the battery the switch operable for closing an electrical circuit with the circuit board via the conductor.

* * * * *